United States Patent [19]

Venturello et al.

[11] Patent Number: 5,268,472

[45] Date of Patent: * Dec. 7, 1993

[54] NITROGEN CONTAINING HETEROCYCLIC PEROXYACID

[75] Inventors: Carlo Venturello, Novara; Claudio Cavallotti, Milan; Fiorella Achilli, Agazzano, all of Italy

[73] Assignee: Ausimont S.p.A., Italy

[*] Notice: The portion of the term of this patent subsequent to Dec. 10, 2008 has been disclaimed.

[21] Appl. No.: 956,567

[22] Filed: Oct. 5, 1992

Related U.S. Application Data

[63] Continuation of Ser. No. 603,101, Oct. 25, 1990, abandoned, which is a continuation of Ser. No. 346,520, May 2, 1989, abandoned.

[30] Foreign Application Priority Data

May 4, 1988 [IT] Italy ................................ 20456 A/88

[51] Int. Cl.$^5$ ................. C07D 233/04; C07D 211/60; C07D 207/04
[52] U.S. Cl. ..................................... 540/610; 546/227; 546/228; 546/245; 548/531; 548/532; 548/533; 548/535; 548/536
[58] Field of Search ................. 540/610; 546/227, 228, 546/245; 548/531, 532, 533, 535, 536

[56] References Cited

FOREIGN PATENT DOCUMENTS 0056699 7/1982 European Pat. Off. .
0082738 6/1983 European Pat. Off. .
0233476 8/1987 European Pat. Off. .

OTHER PUBLICATIONS

*Chemical Abstracts*, 111:23395g (1989) [C. Venturello, et al., EP 300,462, Jan. 25 1989].
*Chemical Abstracts*, 66:47266u (1967) [L. Diamond, et al. Fr. 1,439,351, May 20, 1966].
Houben-Weys "Methoden Der Organischen Chemie" vol. III 1952, p. 38, para. 2, p. 39, para 1.

*Primary Examiner*—Mary C. Lee
*Assistant Examiner*—Joseph K. McKane
*Attorney, Agent, or Firm*—Morgan & Finnegan

[57] ABSTRACT

Nitrogen-containing heterocyclic (poly) peroxycarboxylic acid monopersulfates which have the formula:

$$(R)_m \underset{\underset{R^1}{\overset{|}{N}}}{\diagdown} (CH_2)_n \diagdown C-OOH \atop \overset{\|}{O} \cdot H_2SO_5 \qquad (I)$$

wherein the symbols have the following meanings:

R represents a hydrogen atom or an alkyl, (hetero)cycloalkyl, (hetero)aryl, alkyl-aryl or arylalkyl group, wherein said groups are optionally substituted, or a carboxylic group or a peroxycarboxylic group, or any other substituents non-reactive in the presence of the peroxycarboxylic group;
$R^1$ represents an alkyl group > $C_5$;
n is a number selected from 0,1 and 2;
m is a number selected from 1, 2 and 3;

and the heterocyclic ring may be in its turn condensed with at least one further (hetero) aromatic or (hetero)-cycloalkylic ring. The invention relates to a preparation process for, and to their use, as bleaching agents.

5 Claims, No Drawings

NITROGEN CONTAINING HETEROCYCLIC PEROXYACID

This is a continuation of co-pending application Ser. No. 07/603,101, filed on Oct. 25, 1990, now abandoned, which is a continuation of application Ser. No. 07/346,520 filed on May 2, 1989, now abandoned.

DESCRIPTION OF THE INVENTION

The present invention relates to per se new organic (poly)peroxyacid monopersulfates which may be referred to as nitrogen-containing heterocyclic (poly)-peroxycarboxylic acid monopersulfates, and to their relevant preparation process.

In particular, the present invention relates to nitrogen-containing heterocyclic (poly)peroxycarboxylic acid monopersulfates having the formula (I):

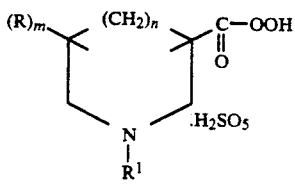

wherein the symbols have the following meanings:
R represents a hydrogen atom or an alkyl, (hetero)cycloalkyl, (hetero)aryl, alkylaryl or arylalkyl group, wherein said groups are optionally substituted, or a peroxycarboxylic group, or any other substituent non-reactive in the presence of the active oxygen of the peroxycarboxylic group;
$R^1$ represents an alkyl group $> C_5$;
n is a number selected from 0, 1 and 2;
m is a number selected from 1, 2 and 3; and the heterocyclic ring may in its turn be condensed with at least one further (hetero) aromatic or (hetero)cycloalkylic ring;
to their preparation process, and to their use as bleaching agents.

The nitrogen-containing heterocyclic peroxycarboxylic monopersulfate compounds having the above formula (I) are per se novel, and constitute a new class of highly interesting products form an industrial viewpoint, with particular reference to their high content of active oxygen per unit weight.

They, in fact, may be used similarly to the already known peroxyacids in the field of plastics materials as monomer polymerization initiator agents, and, in particular, as oxidizing agents for olefin epoxidation and hydroxylation, and in many other oxidative processes in the field of fine chemistry.

In a more specific way, however, the nitrogen-containing heterocyclic (poly)peroxycarboxylic acid monopersulfates having the above formula (I) find a particularly efficacious application in the field of bleaching, in the detergent industry.

In past years, the organic peroxyacids aroused an increasing interest in the industrial field, due to their excellent possibilities for use as bleaching agents in compositions for medium low temperature washing, as well also as due to energy-saving considerations.

Therefore a considerable research activity exists aiming to discover organic peroxyacid compounds endowed with the necessary requisites of bleaching activity, thermal stability, and storage stability or shelf life; these latter requisites being essential for industrial uses and for the widespread application of such compounds.

Therefore many either mono- or di-peroxycarboxylic, straight or cyclic, organic peroxyacids are known and used, among others, in the field of detergents.

Already described peroxycarboxylic acids are, e.g.: diperoxydodecanedioic acid, monoperoxyphthalic acid, diperazelaic acids, substituted diperoxyglutaric and adipic acids, etc.

The conventional preparation process contemplates carrying out the oxidation of the substrate with a solution of hydrogen peroxide in concentrated $H_2SO_4$.

The above method, when applied to substrates containing salifiable nitrogen atoms of basic character, confers on the same substrate a high solubility in the strongly acid medium. This high solubility makes it impossible to apply any of the traditional processes of isolation of the peroxycarboxylic acid derivative which may be formed, such as precipitation and extraction with an organic solvent.

Surprisingly, it has been discovered in accordance with the present invention that the nitrogen-containing heterocylic (poly)peroxycarboxylic acid monopersulfates having the formula (I), salified on the nitrogen atom with the persulfuric anion, may be obtained in a stable form by means of a novel process, which is also the subject matter of the present invention.

Therefore, an object of the present invention is to provide, as per se novel compounds, the nitrogen-containing heterocyclic (poly)peroxycarboxylic acid monopersulfates having the above formula (I).

Another object of the present invention is to provide a simple and cheap process for the preparation of the above peroxycarboxylic acids derivatives having the above formula (I) in a per se stable form.

A further object of the present invention is the use of the nitrogen-containing heterocyclic peroxycarboxylic acid monopersulfates having the above formula (I) as bleaching agents in detergent formulations; in particular those destined for low-medium temperature use.

These, and still other objects which will become even clearer for those skilled in the art from the following detailed disclosure, are achieved, according to the present invention, by the nitrogen-containing heterocyclic peroxycarboxylic acid monopersulfates having the above formula (I), and by the relevant preparation process, characterized in that a substrate constituted by a nitrogen-containing heterocyclic (poly)carboxylic acid or its N-sulfate salt, corresponding to the desired peroxycarboxylic acids having formula (I), is reacted with $H_2O_2$ in concentrated $H_2SO_4$ and in that the peroxycarboxylic acid (I) is then separated from the reaction mixture by means of the addition of an organic solvent selected from tetrahydrofuran and ethyl acetate.

In this way, peroxycarboxylic acids having the formula (I) are obtained, generally as stable solids, salified on their nitrogen atom with persulfuric anion, by their insolubilization in the reaction medium by the solvent.

Defined in a somewhat more explicit way, the process according to the present invention consists or consists essentially in the peroxycarboxylation reaction of the substrate consisting or consisting essentially of the (poly)acid, or its N-sulfate corresponding to the desired acid of formula (I), in an acid medium by concentrated $H_2SO_4$ with $H_2O_2$ and in the subsequent addition, at reactions' end, of a suitable organic solvent, which is not miscible with the desired product by dissolving it, and which is capable, on the contrary, of completely dissolving the acid reaction medium (concentrated $H_2SO_4$), as well as the excess of $H_2O_2$ with the reaction water. This involves the consequent separation, by insolubilization, of the (poly)peroxycarboxylic acid product having the formula (I), which precipitates, usually, in a stable solid form.

The obtained product is then filtered, washed with the solvent, dried, and so forth, according to per se known techniques.

As stated, the substrate used as the starting material is constituted by the nitrogen-containing heterocyclic (poly)carboxylic acid or by its N-sulfate corresponding to the desired (poly)peroxycarboxy acid monopersulfate of formula (I); these compounds are per se known and/or may be prepared according to per se conventional techniques.

Referring to the above formula (I), R is constituted by a linear or branched alkyl, (hetero)-aryl, (hetero)-cycloalkyl, alkyl-aryl or aryl-alkyl group, containing an overall number of up to 10 carbon atoms, and, in the heterocyclic rings, N atoms or O atoms may be present. These groups may in turn be substituted with one or more atoms or groups, either equal to, or different from, one another, inert under the reaction conditions under which the reaction takes place, such as, e.g., F, Cl, $NO_2$ groups, lower $C_1$-$C_5$ alkoxy groups, and so forth.

As an alternative, R is constituted by any other substituent which does not react with the active oxygen of the peroxycarboxylic group, e.g., a carboxylic group, a peroxycarboxylic group, an F atom, a Cl atom, an $NO_2$ group, lower ($C_1$-$C_5$)-alkoxy groups, and so forth.

$R_1$ represents an alkyl group containing more than 5 carbon atoms, and preferably between 8 and 20 carbon atoms.

Finally, the heterocyclic ring may be condensed with at least one (hetero) aromatic or (hetero) cycloalkyl ring, e.g. in the form of an quinolinic, isoquinolinic, pyrido-indolic group, and so forth.

The number n is preferably equal to 1, when R is a H atom.

Suitable substrates are proved to be, as examples, N-octyl-4-piperidine carboxylic acid, N-decyl-4-piperidinecarboxylic acid, and N-hexadecyl-4-piperidinecarboxylic acid.

In case R=COOH, preferably in a non-ortho-position with respect to the nitrogen atoms, the peroxycarboxylation of R may be carried out also, thus obtaining a product of formula (I) with two or more peroxycarboxylic groups.

According to a preferred operating mode, the peroxycarboxylation of the nitrogen-containing heterocyclic (poly)carboxylic acids used as the starting substrate is carried out by gradually adding $H_2O_2$, having a concentration within the range of from approximately 70% to approximately 90% by weight, to a solution of the substrate in concentrated $H_2SO_4$ (96-98%) by maintaining the reaction temperature throughout the reaction at values of about 20° C.

As an alternative, it has been found that it is possible to proceed to the previous preparation of the salified (sulfate) substrate as an $H_2SO_4$ salt, by operating in the absence of $H_2O_2$, under the same conditions as above described, and by separating the obtained salt which is then peroxidated.

The amount of $H_2SO_4$ determined at a concentration of 100%, is at least 5 moles per each substrate mole, and is preferably between approximately 6 and 14 moles.

The hydrogen peroxide is used in an amount which is in excess with respect to the substrate, and equals at least 5 moles per each substrate mole.

The reaction time depends on the nature of the substrate, on the operating temperature, and on the end total $H_2SO_4/H_2O$ molar ratio present at the end of the reaction. Said ratio is between approximately 1.3 and 4 obtained by adjusting the various involved parameters.

Reaction times between approximately 30 minutes and 1 hour have been demonstrated to be operative.

The amount of tetrahydrofuran or ethyl acetate solvent used is usually not lower than 4 liters/substrate mole, such as, for example 7 liters/mole; furthermore, it is added at a temperature not higher than approximately 10° C.

The nitrogen-containing heterocyclic peroxycarboxylic acid monopersulfates having formula (I) are usually solid at room temperature. They may be particularly used in the formulation of detergent compositions, e.g., granular formulations, as bleaching agents in solution within a wide temperature range, owing to their characteristics of good storage stability and good thermal stability.

The detergent compositions may be formulated according to the usual pertinent techniques, together with the other components and/or additives, etc.

The present invention will now be described in greater detail in the following examples, which are supplied for purely illustrative purposes.

The products prepared in the examples were characterized by elemental analysis, by determining their content of active oxygen (by iodometric titration), and by using Fourier Transform Infrared Spectroscopy (FT-IR).

EXAMPLE 1

5.1 g (0.019 mole) of N-decyl-isonipecotic acid were completely dissolved at +35° C. into 11.6 g of $H_2SO_4$ at 96% (0.114 mole).

3.8 g of $H_2O_2$ at 85% (0.095 mole) were then added to the solution so that the temperature was maintained at about +15° C.

The stirring was then continued for 45 minutes at +15° C.

The reaction mixture was then poured into 140 ml of ethyl acetate maintained under stirring at −10° C. After 30 minutes, the separated crystalline was filtered under vacuum over a porous septum and was directly washed on the filter with ethyl acetate (2×30 ml), then with ethyl ether (2×30 ml). The product was then kept inside a $CaCl_2$-drier under vacuum and at room temperature for 1 hour.

4.8 g of crystalline N-decyl-piperidine-4-percarboxylic acid monpersulfate were obtained having an active oxygen content of 7.8% (97.4% of the theoretic value). Yield: 62%.

Elemental Analysis:

computed for $C_{16}H_{33}NSO_8$: C, 48.10%; H, 8.32%; N, 3.50%; 0 (active) 8.01%; $H_2SO_5$, 28.55%.

Found: C, 48.06%; H, 8.41%; N, 3.49%; 0 (active), 7.80%; $H_2SO_5$, 28.5%.

Melting point: 78° C. (with decomposition).

EXAMPLE 2

4 g (0.0113 mole) of hexadecyl-4-piperidin-carboxylic acid were slowly added under stirring to 2.5 g of sulphuric acid in a 25 ml beaker, care being taken to maintain the temperature at about 40° C. by the use of a cooling bath, the stirring was being continued at 35°–40° C. for 2 hours.

The reaction mixture was then poured into 150 ml of ethyl acetate maintained under stirring at 10° C. The stirring was continued for 30 minutes.

The separated hexadecyl-4-piperidin-carboxylic acid sulphate was filtered over a porous septum, washed first with ethyl acetate (2×30 ml), then with $Et_2O$ (2×30 ml), then dried under vacuum at room temperature over $CaCl_2$.

4.1 g of product were obtained, which was used for preparing the corresponding peracid monpersulfate.

2 g of $H_2O_2$ at 85% (0.05 mole) were added under stirring to 12 g of $H_2SO_4$ at 96% (0.1175 mole) by maintaining the isothermy within +5° C. 4.1 g of N-hexadecyl-isonipecotic acid sulphate (0.0091 mole) were added so as to maintain the temperature not higher than 15° C. The reaction mixture was poured into 100 ml of ethyl acetate maintained under stirring at −10° C. It was carried out according to Example 1.

3.2 g of crystalline, practically pure N-hexadecyl-piperidine-4-percarboxylic acid monopersulfate were obtained.

Yield: 73%

Elemental Analysis

Computed for $C_{22}H_{45}NSO_8$: C, 54.63%; H, 9.37%; N, 2.89%; 0 (active), 6.61%; $H_2SO_5$, 23.58%.
Found: C, 53.9%; H, 9.35%; N, 2.89%; 0 (active), 6.6%; $H_2SO_5$, 23.41%.
Melting point: 84° C. (with decomposition).

EXAMPLE 3 (Application example)

Bleaching tests were carried out with a novel nitrogen containing heterocyclic peroxyacid monopersulfate reported in the herewith enclosed Tables 1 and 2 below at alkaline pH (Table 1) and at acid pH (Table 2), in comparison to:

H 48 (Mg salt of monoperphthalic acid), a commercial peroxyacid known in the field of detergence, manufactured by INTEROX Chemical Ltd., London, U.K. (Tables 1 and 2).

All tests were carried out at the constant temperature of 60° C., with an initial concentration of total active oxygen in the bleaching equal for all products, and equal to 200 mg/l.

Process

For each test, 500 ml of deionized water, contained inside a 1,000 ml flask equipped with a condenser, was heated to a temperature of 60° C. and to a pH value of 9.5 (with NaOH) (Table 1) and to a pH value of 3–4 (with a few drops of diluted $H_2SO_4$) (Table 2); then the bleaching product was added with stirring with such amounts thereof being added as shown in the following Table, and immediately after two cotton specimens of 10 cm × 10 cm stained with standard stains of red wine at EMPA INSTITUTE of St. Gallen (Switzerland), and marked by "EMPA 114" mark, were added.

The system was subsequently kept stirred for 60 minutes and, at the end of this time, the specimens, rinsed under running water, were dried and ironed, and were then subjected to the evaluation of bleaching effect by means of measurements of degree of white by reflectometry; the results are reported in following Tables 1 and 32, wherein the data is expressed as Bleaching %, defined as:

$$\text{Bleaching \%} = \frac{A - B}{C - B} \times 100$$

wherein:
A = degree of white (%) of the specimen bleached, after the test;
B = degree of white (%) of the specimen before the test;
C = degree of white (%) of the completely bleached specimen, and wherein the degrees of white were measured by an Elrepho Zeiss reflectometer, assuming MgO = 100% white, and using filter N.6 ( =464 mm).

The data in Table 1, showing tests at alkaline pH, evidence that the novel peroxy acids have a bleaching power comparable with that of H 48.

Likewise, the results, expressed as Bleaching %, reported in Table 2, shown that the products have a bleaching power in an acid solution particularly high and indeed higher than the bleaching power of H 48.

These results are particularly surprising considering that the peroxyacid compounds generally show a bleaching activity that is very modest and sometimes negligible at acid pH.

| COMPOUND | Amounts used in the test (grams) | Initial concentration of total active oxygen (mg/l) | Bleaching (%) |
|---|---|---|---|
| EXAMPLE 1 (titer = 5.50% of active oxygen) | 1.28 | 200 | 74.18 |
| H 48 (titer = 5.5% of active oxygen) | 1.86 | 200 | 81.0 |

TABLE 2

| | Tests at acid pH (3-4) | | |
|---|---|---|---|
| COMPOUND | Amounts used in the test (grams) | Initial concentration of total active oxygen (mg/l) | Bleaching (%) |
| EXAMPLE 1 (titer = 7.80% of active oxygen) | 1.28 | 200 | 78.4 |
| H 48 (titer = 5.5% of active oxygen) | 1.86 | 200 | 60.0 |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

What is claimed is:

1. Nitrogen-containing heterocyclic (poly)peroxycarboxylic acid monopersulfates having the formula:

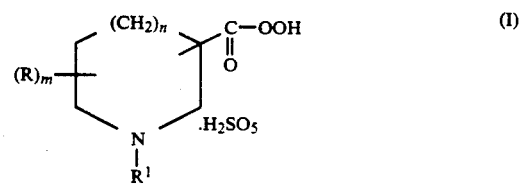

wherein:
  R represents a hydrogen atom; an alkyl, alkylaryl, or arylalkyl group containing up to 10 carbon atoms, said group being optionally substituted with F atom, Cl atom, $NO_2$ group, lower $C_1$–$C_5$ alkoxy group; carboxylic group or peroxycarboxylic group;
  $R^1$ represents an alkyl group having more than 5 carbon atoms;
  n is a number selected from 0, 1 or 2; and,
  m is 1, 2, or 3.

2. Nitrogen-containing heterocyclic (poly)peroxycarboxylic acid monopersulfate according to claim 1, wherein n is 1 and R is a hydrogen atom.

3. (Poly) peroxycarboxylic acid monopersulfate according to claim 1, wherein the heterocyclic ring is constituted by a ring condensed with at least one other (hetero) aromatic or (hetero) cycloalkyl pyridine ring, 4. As a compound: N-decyl-piperidine-4-percarboxylic acid monopersulfate.

5. As a compound: N-hexadecyl-piperidine-4-percarboxylic acid monopersulfate.

* * * * *